(12) United States Patent
Delorme et al.

(10) Patent No.: US 8,328,825 B2
(45) Date of Patent: *Dec. 11, 2012

(54) METHOD AND IMPLANT FOR CURING CYSTOCELE

(75) Inventors: Emmanuel Delorme, Chalon sur Saone (FR); Georges Eglin, Beziers (FR); Jean-Marc Beraud, Saint-Etienne (FR)

(73) Assignee: Coloplast A/S, Humlebaek (DK)

( * ) Notice: Subject to any disclaimer, the term of this patent is extended or adjusted under 35 U.S.C. 154(b) by 579 days.

This patent is subject to a terminal disclaimer.

(21) Appl. No.: 12/339,478

(22) Filed: Dec. 19, 2008

(65) Prior Publication Data

US 2009/0118571 A1     May 7, 2009

Related U.S. Application Data

(63) Continuation of application No. 10/809,798, filed on Mar. 26, 2004, now Pat. No. 7,494,495.

(51) Int. Cl.
*A61B 17/08* (2006.01)
*A61F 2/00* (2006.01)

(52) U.S. Cl. ......................................... 606/151; 600/37

(58) Field of Classification Search .................. 606/151, 606/193; 600/29, 30, 37; 128/885; 623/11.11, 623/23.64–23.67
See application file for complete search history.

(56) References Cited

U.S. PATENT DOCUMENTS

| | | | | | |
|---|---|---|---|---|---|
| 2,199,690 | A | * | 5/1940 | Bullard | 128/207.11 |
| 3,384,073 | A | * | 5/1968 | Van Winkle, Jr. | 600/30 |
| 3,981,305 | A | * | 9/1976 | Ring | 604/15 |
| 5,481,763 | A | * | 1/1996 | Brostrom et al. | 2/452 |
| 5,785,640 | A | * | 7/1998 | Kresch et al. | 600/29 |
| 5,840,011 | A | * | 11/1998 | Landgrebe et al. | 600/30 |
| 6,203,572 | B1 | * | 3/2001 | Johnson et al. | 623/13.15 |
| 6,251,143 | B1 | * | 6/2001 | Schwartz et al. | 623/23.72 |
| 6,423,080 | B1 | * | 7/2002 | Gellman et al. | 606/148 |
| 6,638,210 | B2 | * | 10/2003 | Berger | 600/30 |
| 6,776,161 | B2 | * | 8/2004 | Horn | 128/207.11 |
| 6,808,487 | B2 | * | 10/2004 | Migliari | 600/30 |
| 7,131,943 | B2 | * | 11/2006 | Kammerer | 600/30 |
| 7,131,944 | B2 | * | 11/2006 | Jacquetin | 600/30 |
| 2001/0010023 | A1 | * | 7/2001 | Schwartz et al. | 623/23.72 |
| 2002/0055748 | A1 | * | 5/2002 | Gellman et al. | 606/139 |
| 2002/0099259 | A1 | * | 7/2002 | Anderson et al. | 600/29 |
| 2003/0004395 | A1 | * | 1/2003 | Therin | 600/37 |
| 2003/0220538 | A1 | * | 11/2003 | Jacquetin | 600/37 |
| 2004/0039453 | A1 | * | 2/2004 | Anderson et al. | 623/23.72 |
| 2004/0116774 | A1 | * | 6/2004 | Migliari | 600/37 |

* cited by examiner

*Primary Examiner* — Dianne Dornbusch

(74) *Attorney, Agent, or Firm* — Coloplast Corp., Coloplast A/S; Daniel G. Chapik; Nicholas R. Baumann

(57) ABSTRACT

An implant for the treatment of cystocele, having a thin and supple structure, comprises a support body (2) from which extend at least two anterior suspension straps (3) arranged on both sides of the sagittal plane (S), two posterior suspension straps (4), arranged on both sides of the sagittal plane (S), and two middle suspension straps (5) arranged on both sides of the sagittal plane (S) and between the anterior and posterior straps (3) and (4).

28 Claims, 3 Drawing Sheets

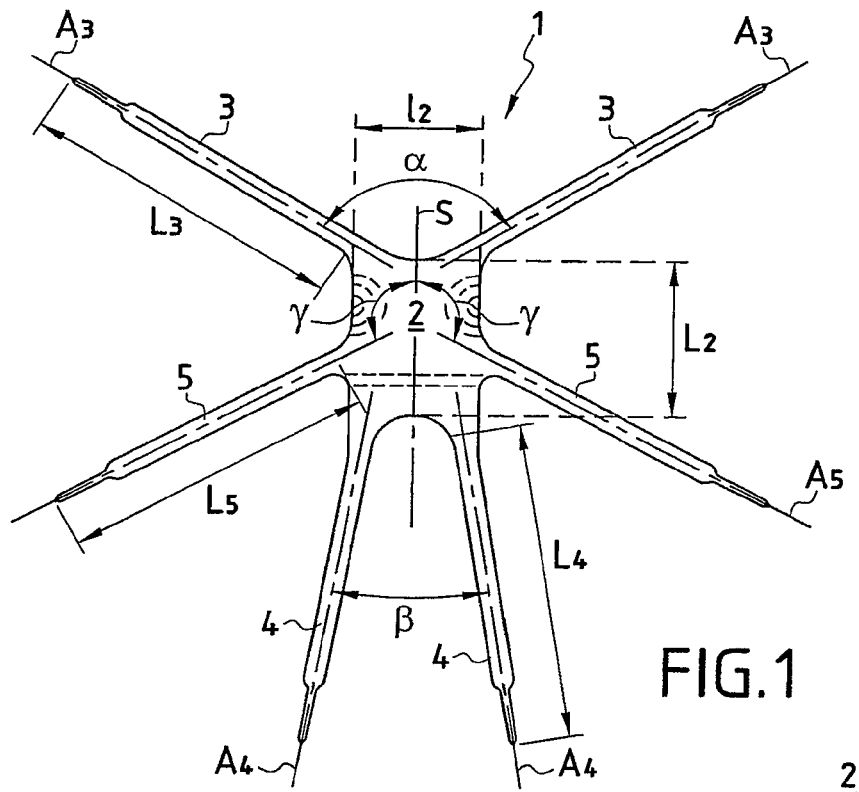
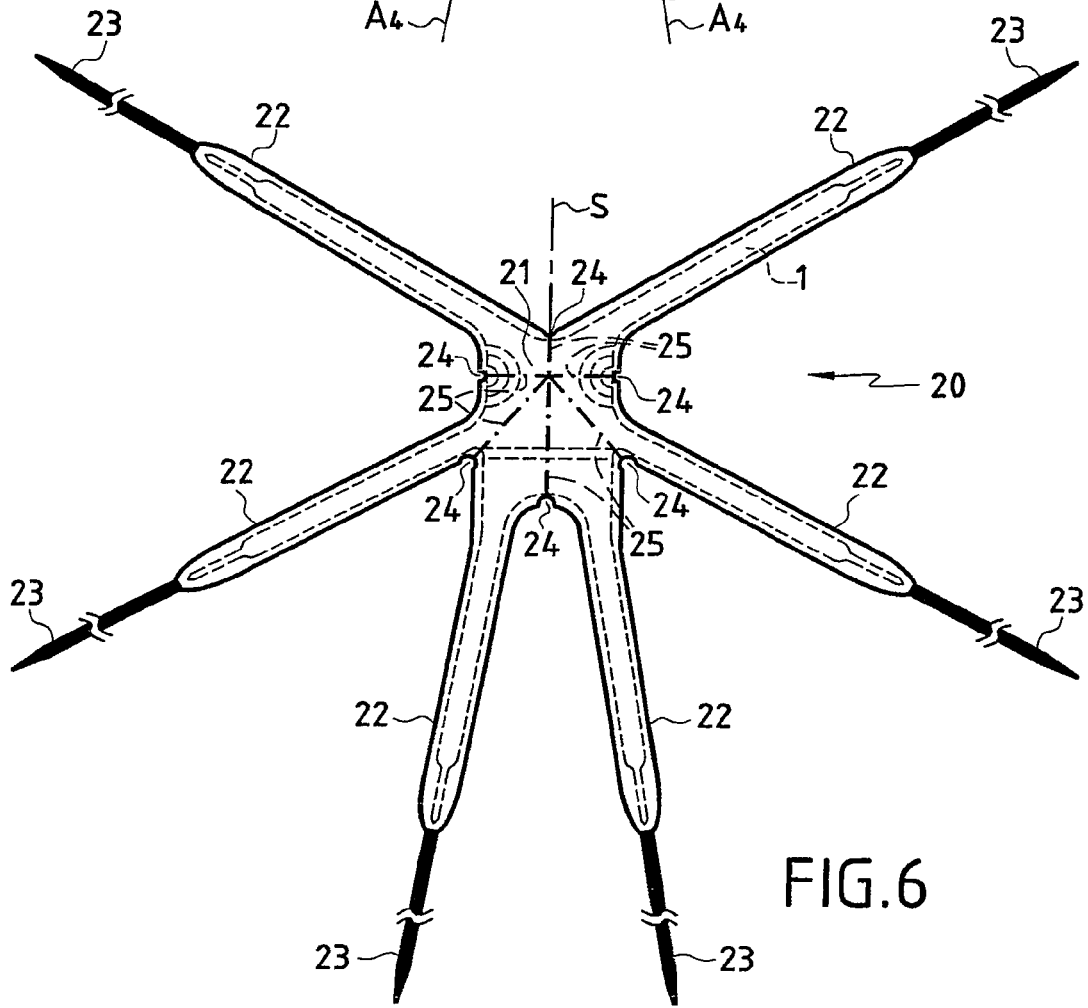

METHOD AND IMPLANT FOR CURING CYSTOCELE

CROSS REFERENCE TO RELATED APPLICATION

The present application is a continuation of non-provisional application Ser. No. 10/809,798 filed on 26 Mar., 2004, now U.S. Pat. No. 7,494,495, the entirety thereof being incorporated herein by reference thereto.

FIELD OF THE INVENTION

The present invention concerns the technical field for the treatment of cystocele, in particular in the elderly woman.

BACKGROUND OF THE INVENTION

In general, cystocele phenomena result from the slackening of the suspension tissue of the urinary and genital organs, provoking disorders that require surgery.

Thus, it has been provided attempts to reconstruct the natural system for the suspension of organs affected by this slackening, implementing non-resorbent suture or reinforcement strips. However, these techniques are not always satisfactory, in particular due to the requirement for a heavy surgical intervention, inducing a dissection of the anatomic regions not involved by the surgical repair for the non-resorbent sutures.

So as to try to overcome these drawbacks the patent application FR 2 785 521 provides an implant wherein a support body from which two suspension cords at the end of which anchoring elements intended to form sutures on regions considered to be anatomically stable. This implant is then inserted by laparoscopy, thereby reducing the surgical procedure.

However, such an implant has not been able for providing effective suspension, mainly due in particular to the stress applied to the regions considered to be anatomically stable. In addition, this type of implant does not have great stability in space in the conditions of use.

Therefore, the need appeared for an implant providing on one hand, better implant insertion stability and on the other hand, a technique that provides optimum stability while providing a maximum reduction of the patient's trauma.

SUMMARY OF THE INVENTION

Thus, in order to achieve these objectives, the invention concerns an implant for the treatment of cystocele, presenting a thin and supple structure and comprising a support body from which two anterior suspension straps extend on both sides of a sagittal plane of the support body and two posterior suspension straps extend on both sides of the sagittal plane.

According to an essential characteristic of the invention, the implant also comprises so-called middle suspension straps, extending from the support body on both sides of the sagittal plane and between the anterior and posterior straps.

The implementation of six suspension straps then provides better distribution of the effort acting on the support body on the anatomic anchoring points of the straps, while guaranteeing better orientation in space of the support body implanted in the patient.

According to a preferred but not strictly necessary characteristic of the invention, the anterior suspension straps are each intended to be fitted in one of the two ischeo-pubic foramen still called obturators or obturated foramen and, for this purpose, having a length exceeding 100 mm and, preferably, exceeding 120 mm.

According to another characteristic of the invention, the longitudinal axes of the anterior straps form an angle a exceeding 45° and, preferably but not strictly necessarily, an angle $\alpha$ between 100° and 180° and, preferably between 115° and 170. It should be noted that according to a preferred embodiment of the invention, the sagittal plane forms an axis of symmetry of the implant and thereby bisecting the angle $\alpha$.

According to another characteristic of the invention, the longitudinal axes of the posterior straps form an angle $\beta$ that is not zero. Thereby, the posterior straps are not to be considered to be parallel. Preferably, but not strictly necessarily, the angle $\beta$ exceeds 10° and is preferably between 10° and 75° or even between, 100° and 180° according to the disorder treated.

Preferably, the length of the posterior straps exceeds 100 mm and preferably 120 mm.

According to another characteristic of the invention, the middle suspension straps also exceed 100 mm and, preferably 120 mm.

According to another preferred but not strictly necessary characteristic of the invention, the shape of the support body is substantially rectangular. In a preferred but not strictly necessary characteristic, the support body is between 60 mm and 90 mm long and between 40 mm and 60 mm wide.

According to a preferred embodiment of the invention, the anterior straps substantially extend from the anterior corners of the support body and the posterior straps also extend from the posterior corners of the support body.

The invention also concerns a surgical technique for the insertion of said implant and the treatment of cystocele.

According to the invention, the main characteristic of this technique consists in inserting each one of the anterior suspension straps into one of the ischio-pubic foramen, also known as obturators or obturated foramen.

As for the middle suspension straps they are each placed either in the middle translevator region, or into an obturated foramen in its infero-posterior region.

The posterior straps are either trans-fixed in the uterosacral ligaments or placed across the uterosacral ligaments then in the transgluteai region, preferably but not exclusively across the sacrosciatic ligaments.

It should be noted that, according to this technique, the hold is mainly provided by friction between the implant and the tissues crossed and, more specifically, by friction between the suspension arm and the muscle tissue crossed.

Preferably, this technique is embodied during so-called mini-invasive surgery, using approach routes in the vicinity of the organs to treat, so as to reduce the time of surgery and blood loss. It is thereby possible to obtain a short post-surgical period with minimum patient discomfort. In addition, the simplicity of this technique makes it easy to reproduce and reduces the training required by surgeons.

The invention also concerns an introduction device that may be used without it being absolutely necessary according to the meaning of the invention for the insertion of the implant as disclosed above.

The introduction device according to the invention comprises an introduction member with a supple structure and a shape similar to that of the implant and which comprises:
  a hollow body defining a cavity for the reception of the body of the implant,
  tubular branches extending from the hollow body, each defining a cavity for the reception of an implant suspension strap, means of traction extending from the end of each branch of the introduction member, and means for cutting at least the hollow body of the introduction member.

According to one characteristic of the invention, the means of traction comprise a semi-rigid needle for each tubular branch.

According to the invention, the means for cutting may be implemented in any appropriate way, such as for example, through a line of lesser resistance likely to break when a traction is carried out at both tubular branches opposite of the introduction member.

According to a preferred but not strictly necessary characteristic of the invention, the means for cutting comprise at least one aperture for the passage of a cutting tool. Preferably, the body of the introduction member comprises a series of apertures located close to a line corresponding to the sagittal plane of the implant as well as between the tubular branches.

According to another characteristic of the invention, the introduction device comprises an implant in accordance with the invention, placed in the cavity of the hollow body and the tubular branches of the introduction member. Preferably but not strictly necessarily, the implant is free inside the introduction member.

To facilitate the surgeon's work, according to another characteristic of the invention, the introduction device also comprises at least an ancillary surgical material that comprises an elongated perforator guide or trocar whose end is intended to be introduced in the body of the patient, the other end of which is fitted with a handle.

According to a characteristic of the invention, the perforator guide is curved in one plane. Preferably, but not strictly necessarily, the curved shape of the perforator extends over an angular sector exceeding 140° and, preferably but not necessarily, inferior to 180° and, preferably, between 150° and 170°. Preferably, the curved portion of the perforator guide is then curved with a radius of between 30 mm and 60 mm and, preferably, for the portion of the perforator guide extending from the handle to the end intended to be introduced in the patient's body of between 40 mm and 50 mm, the outer part of the perforator is then curved with a variable radius.

According to another characteristic of the invention, the perforator guide has a helicoid shape at the opposite end of the handle or distal end. Preferably, the perforator guide then has the shape of a portion of helicoid spire extending over an angle of between 180° and 360° and, preferably, between 255° and 270°. Similarly, the spire of the perforator guide has preferably a radius of curvature between 20 mm and 40 mm, with a pitch between 15 mm and 25 mm.

According to another characteristic of the invention, to reduce the trauma that the patient's body undergoes during the introduction of the implant, the introduction device also comprises a tubular casing whose shape is complementary to that of the perforator guide. This tubular casing is then made to be fit on the perforator guide and to remain in the patient's body after removal of the perforator guide to define a tunnel for the passage of the means of traction of the introduction member. The tubular casing is then removed, after passage of the means of traction when the introduction device is removed.

According to the invention, the tubular casing may be made of any supple biocompatible material such as, for example, but not exclusively, PVC.

Different other characteristics of the invention follow from the above description with reference to the appended drawings that illustrate different embodiments of the implant according to the invention, as well as introduction members making the insertion of the said implant possible.

Moreover, it should be noted that the different characteristics of the invention disclosed above and hereafter, may be combined in different alternatives, with relation to the disorder to treat.

BRIEF DESCRIPTION OF THE DRAWINGS

FIG. 1 is an elevation front view of an implant according to the invention, more particularly intended for the treatment of cystocele.

FIG. 6 is a view of an introduction member according to the invention, enabling the insertion of the implant shown in FIG. 1.

DETAILED DESCRIPTION OF THE INVENTION

Figure 2:
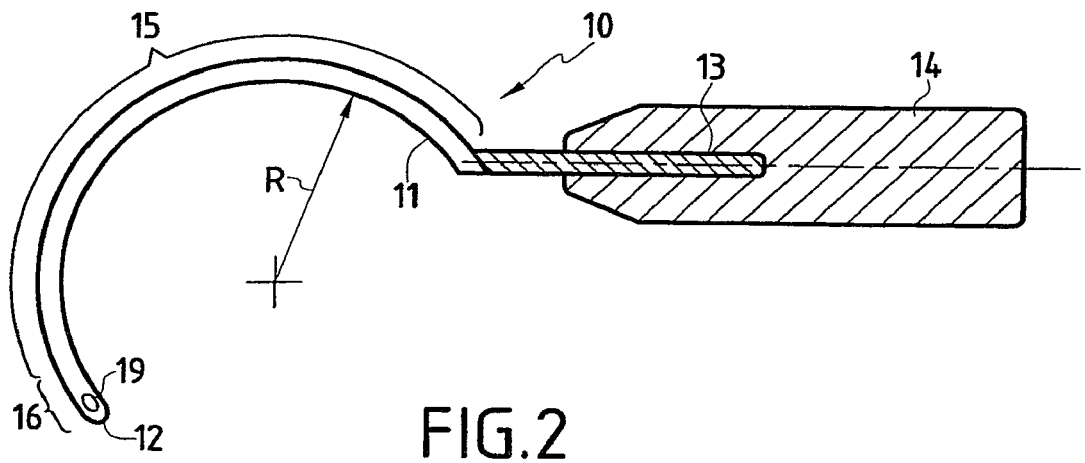
FIG. 2 is an elevation view, partially removed, of a perforator guide that may be used for the insertion of an implant according to the invention with a curved shape.

A preferred application of the invention is for the treatment of cystocele. For this purpose, the invention proposes an implant more particularly designed for this disorder and on the whole indicated by reference 1 in FIG. 1. The implant 1 has a thin and supple structure and is made of an adapted bio-compatible material, such as, for example, a synthetic, woven or non woven, or knit material made of polypropylene or polyester fibers. Such a synthetic material may or may not be coated with products favoring cell growth. Similarly, the implant according to the invention, may be made of natural materials such as "fascia latta" or even any biological or synthetic resorbent material.

According to an essential characteristic of the invention, implant 1 comprises a support body 2 from which two anterior suspension straps 3 extend on both side of a sagittal plane S. The implant also comprises two posterior suspension straps 4 also extending on each side of the sagittal plane S. Furthermore, implant 1 comprises two middle suspension straps 5 that extend from the support body 2 on sides of sagittal plane S, between the corresponding anterior straps 3 and posterior straps 4.

According to the example shown, the shape of support body 2 is substantially rectangular, without such a shape being considered as necessary according to the invention and the anterior and posterior suspension straps 3 and 4, each extend from a corner of the body 2. It should be noted that, preferably, sagittal plane S corresponds to a plane of symmetry of implant 1.

According to a preferred characteristic, related to the technique for the implementation provided by the invention, anterior straps 3 are more particularly intended to be introduced in one of the two ischio-pubic foramen of the subject to treat. For this purpose, the longitudinal axes $A_3$ of anterior straps 3 form an angle α, preferably but not necessarily exceeding 45°, preferably between 100° and 180°, preferably between 115° and 170°. In addition, to enable easy insertion of anterior straps 3 in the corresponding ischio-pubic or obturated foramen, the length of the anterior straps $L_3$, measured between the distal end of each anterior strap 3 and support body 2, exceeds 100 mm and preferably is equal to or exceeds 120 mm.

As for the posterior straps 4, and as will appear subsequently, posterior straps 4 are more particularly intended to pass through uterosacral ligaments and, for this purpose, the longitudinal axes $A_4$ of posterior suspension straps 4 form an angle β, preferably but not exclusively not zero, preferably exceeding 10° and, even more preferably, between 10° and 75°. It should be noted that, to facilitate the insertion, the length $L_4$ of posterior suspension straps 4, measured between the distal end of the straps and support body 2, preferably exceeds 100 mm, even more preferably equals or exceeds 120 mm.

As for the middle suspension straps 5, they are intended to be passed across the uterosacral ligaments, and for this purpose, the longitudinal axis $A_5$ of each middle suspension strap 5, forms, along with the anterior part of sagittal plane, an angle γ, preferably but not necessarily of between 100° and 140° and, preferably between 110° and 130° and, in even more preferably, of between 115° and 125°. Such as the other anterior and posterior suspension straps 3 and 4, the length $L_5$ of middle suspension straps 5, measured between the distal end of the middle suspension straps 5 and support body 2, preferably exceeds 100 mm and, more particularly preferably, exceeds or equals 120 mm.

Moreover, the width of suspension straps 3, 4, 5 is chosen, preferably but not exclusively, to be between 5 mm and 15 mm and, for example, about ten millimeters.

Implant 1, as described above, is intended to be inserted in the anterior vaginal wall of a patient. For this purpose, for reducing the dissection of this region and the resulting trauma to a minimum, the invention proposes that the surgeon use one or several elongated perforator guides 10, such as those more particularly shown in FIGS. 2 and 3 to 5.

Such a perforator guide 10 commonly comprises an elongated body or chuck 11, one end 12 of which is intended to be introduced in the body of the subject to be treated and the other end 13 is fitted with a handle 14. It should be noticed that introduction end 12 is preferably formed by a foam tip, that is, a non-traumatic tip that is not likely to wound or cut the tissue in which it has to be introduced.

According to one embodiment shown in FIG. 2, perforator guide 10 is curved in one plane. This curved shape in one plane is especially adapted for the insertion of suspension straps in the anterior and posterior regions of the obturated foramen. Preferably but not strictly necessarily, the curved portion of the perforator guide has a radius of curvature R of between 30 mm and 60 mm and, preferably, for portion 15 of perforator guide 10 extending from handle 14 to end 12, between 40 mm 15 and 50 mm, the outer part 16 of the perforator guide 10 thereby has a variable radius of curvature.

Figure 5:
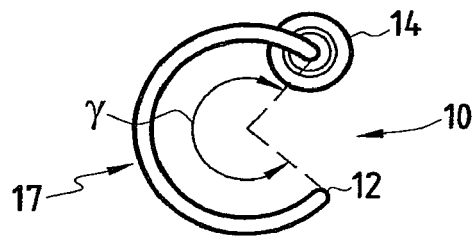
FIG. 5 is a view from below of the perforator illustrated in FIG. 3.
Figures 3, 4:
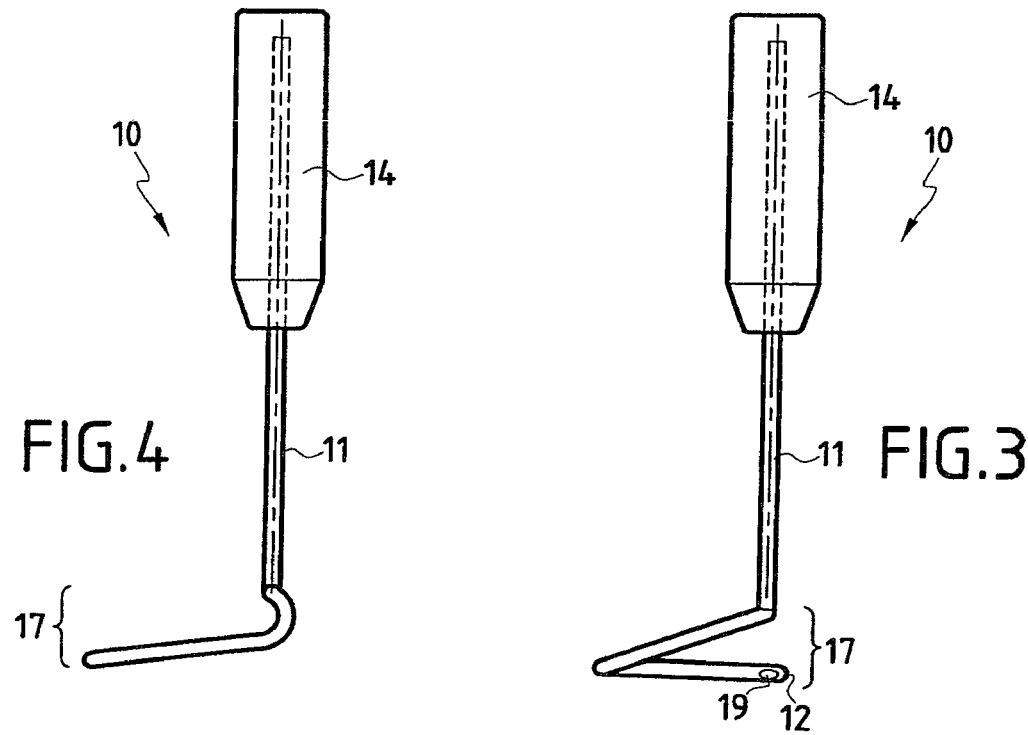
FIG. 3 is an elevation view of another embodiment of a perforator guide according to the invention, with a helicoid-shaped introduction end.
FIG. 4 is a left view of the perforator guide according to FIG. 3.
Figure 7:
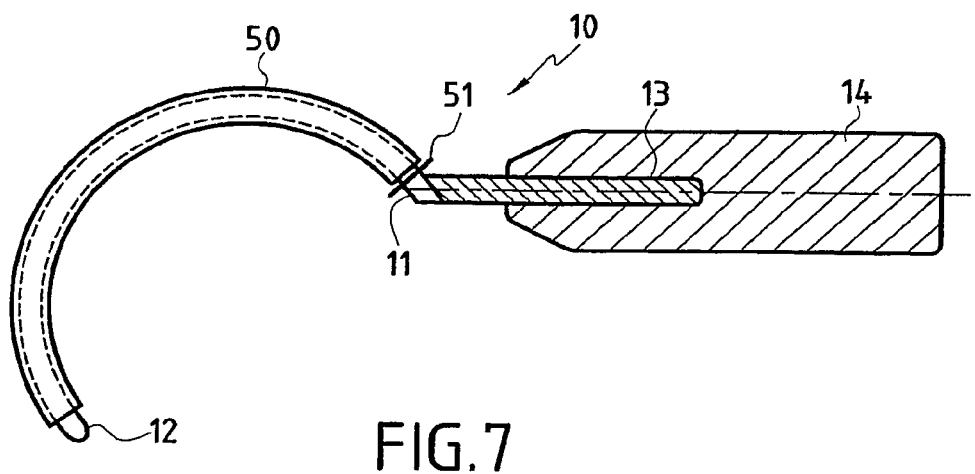
FIG. 7 to 10 are views, similar to FIG. 2 to 3, showing alternatives of the perforator guides for the insertion of an implant according to the invention.
Figure 10:
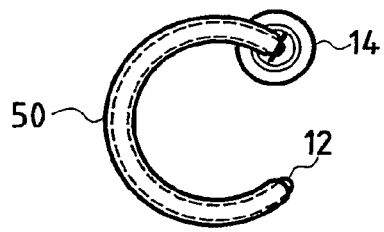
Figure 9:
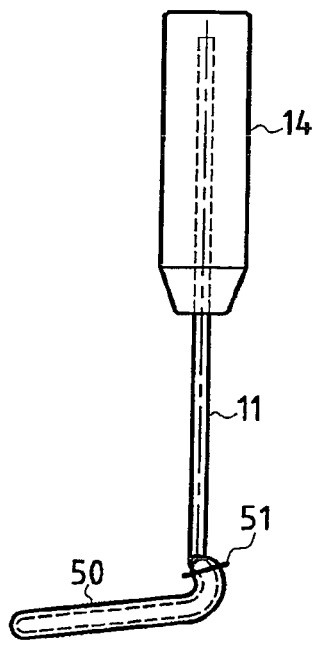
Figure 8:
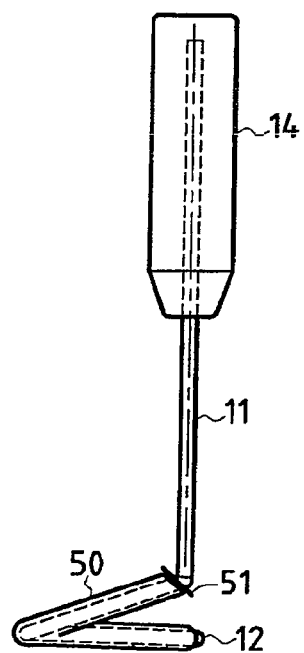

According to another implementation of perforator guide 10, shown in FIG. 3 to 5, the elongated body 11 of guide 10 has a helicoid shaped end 17, also adapted for the insertion of suspension straps in the anterior or posterior regions of the obturated foramen. Preferably, the distal end 17 of the perforator guide thereby has the shape of a portion of helicoid spire extending over an angle γ of between 180° and 360° and, preferably, between 255° and 270°. Also preferably, spire 17 of the perforator guide has a radius of curvature of between 20 mm and 40 mm, with a pitch of between 15 mm and 25 mm.

The surgical treatment of cystocele, by means of an implant 1 and perforator guides 10, as previously described, is carried out as follows.

The patient to be treated is first given an anaesthetic that may be general, regional or even local, according to the preference of the surgeon and the state of health of the patient. The operating position of the patient on the operating table will be that of usual vaginal surgery, that is with the patient's buttocks slightly outside of the surgical table and the thighs slightly bent on the abdomen.

A dissection of the region of intervention is then carried out by respecting the attachments of the bladder neck. Traction is first exerted on the neck of the uterus, for example by means of Muze forceps, in order to expose the anterior fornix of the vagina. A vaginal incision, called horizontal pre-cervical incision, may thereby be carried out on the anterior side of the neck of the uterus, cross-wise on the cervical side of the fornix of the vagina, well exposed by the traction. The entire edge of the anterior vaginal section is then taken hold: vaginal skin and Halban's fascia, by means of, for example, three Alis forceps that are drawn upwards to expose the vesico-vaginal plane. A vesico-vaginal detachment is then progressively carried out by everting the anterior vaginal wall. This detachment is halted at the bottom and in the middle, just above the bladder neck, while it is carried out below and laterally up to the arcatus tendinus fascia pelvis. This area of the arcatus tendinus fascia pelvis is then opened toward the obturator foramen, so as to enable the introduction of a finger behind the obturator muscle. Similarly, the detachment practiced at the top, at the level of the vaginal incision, should enable the introduction of a finger against the levator muscle.

Once the dissection is carried out, the first anterior suspension strap 3 may be inserted in the corresponding ischio-pubic foramen. For this purpose, a curved or helicoid perforator guide 10 is used, as previously described, depending of the surgeon's choice. First, a punctiform incision is carried out preferably about 15 mm outside of the ischio-pubic branch at the horizontal level with respect to the clitoris cap. A finger is then inserted behind the obturator foramen, so as to receive the introduction end or tip 12 of perforator guide 10, introduced by the puctiform incision. Perforator guide 10 is then inserted, led by the finger until the anterior vaginal incision.

At this stage, anterior suspension strap 3 is secured on the perforator guide, for example at the level of an eye 19 at the introduction end 12 of this guide. Once secured, the perforator guide is removed, thereby providing a traction on the anterior suspension strap that is then introduced through the obturator foramen.

The same surgical procedure is repeated for the introduction of the second anterior suspension strap 3.

It should be noted that the anterior suspension straps 3 are preferably positioned without traction to prevent the dysuric effect of implant 1 that is placed just above and behind the bladder neck.

The first middle suspension strap 5 is then put in place.

For this purpose, a punctiform incision is made in the genitocrural groove, horizontally with respect to the posterior commissure of the labia majora. Perforator guide 10 is then introduced by this incision to be led through the levator muscle. It should be noted that the end of perforator guide 10 is then located just within the ischio-public branch, one finger placed against the upper side of the levator muscle receiving the tip of the perforator guide to lead it into the anterior vaginal incision.

The end of middle suspension strap 5 to be placed is then secured at the end 12 of perforator guide 10 which is then removed in the opposite direction to bring along with the middle suspension strap 5.

The same surgical procedure is then repeated for the insertion of the second middle suspension strap 5.

It should be noted that the middle suspension straps 5 are preferably placed, without any traction or mechanical bias, to prevent the cord effect of the fibroid prosthetic strap in the latero-vesicovaginal grooves.

According to an alternative implant, the middle suspension straps 5 may also be implanted through a corresponding obturator foramen, in its lower posterior part opposite to the ischium.

At this stage of the insertion of implant 1, the anterior edge of the implant is preferably secured by one or several, preferably two or three resorbent stitches at the anterior side of the neck of the uterus.

The insertion of implant 1 continues by the entry of posterior suspension straps 4. It should be noticed that the posterior suspension straps 4 are essential in case of hysterectomy without conservation of the neck.

A first posterior suspension strap 4 is placed through the base of the broad ligament and through the base of the uterosacral ligament. For this purpose, perforator guide 10 is introduced from the rear vaginal wall to the front through the uterosacral ligament. Posterior strap 4 is then secured to the perforator guide and drawn in a reverse direction from front to back through the uterosacral ligament.

The same surgical procedure is repeated for the insertion of the second posterior suspension strap 4.

The posterior suspension straps 4 may then be left free after crossing the uterosacral ligaments or on the contrary each be secured by a resorbent suture to the prerectal plate.

According to an alternative of the invention, the posterior suspension straps 4 are each passed first through the corresponding uterosacral ligament, then through the sacrosciatic ligament by means of the perforator guide 10 that will have gone into the transgluteal pathway zone.

The operation finishes with the closing of the vaginal incision by means of resorbent continuous suture as well as the closing of the punctiform incisions also by means of resorbent thread.

At the end of the intervention, a vaginal wick is inserted as well as a bladder probe that are removed forty-eight hours after the intervention. The post-urinary residues are then measured by probe, to make sure that the bladder emptying is satisfactory, so as to authorise the patient's discharge.

The intervention to treat the cystocele lasts about one hour and the average period of hospitalisation is four days. The patient's activity will be restricted for one month and a bath should be avoided during the same period of time. Finally, it is advisable to plan for six weeks of sexual abstinence after the operation.

Therefore, the technique proposed only treats the disorder, that is the imbalance 10 in the pelvic statics and thereby restores as normal an anatomy as possible by preserving the individual's body image. This technique advantageously keeps the healthy organs or does not have an unfavourable effect on the pelvic statics. Indeed, the possibility of cancer will have been eliminated by the pre-surgical assessment and it will be possible to provide reliable gynaecological monitoring after the surgery.

Moreover, there are very low risks of pelvic genital cancer and, in addition, the treatment proposed by the invention does not complicate subsequent access to the genital organs.

As indicated above, the implant according to the invention is preferably inserted so as not to have any residual tension after insertion. To facilitate this surgical procedure, an alternative of the intervention proposes the use of an introduction member, more particularly shown in FIG. 6 and indicated as a whole in reference 20.

This introduction member has a supple structure and its shape is similar to that of the implant. Introduction member 20 is preferably made of a bio-compatible polymer from the family of plastics with a low friction coefficient, such as, for example, polyethylene. Introduction member 20 thereby comprises a hollow body 21 defining a cavity for the reception of body 2 of implant 1. Introduction member 20 also comprises tubular branches 22 that extend from the hollow body 21 and that each define a cavity for the reception of a suspension strap 3, 4 and 5 of the implant 1. Each tubular branch 22 thereby has means of traction 23 extending from the corresponding free end of branch 22. The means of traction 23 may be provided in any appropriate manner such as, for example, systems for the coupling of the ends of branches 22 on a perforator guide 10. According to the example illustrated in FIG. 6, the means of traction 23, comprise for each branch 22, a soft or semi-rigid needle with a nontraumatic or foam tip. Such a needle may be made of the same material as the material used for the introduction device 20 or, more generally, of a biocompatible plastic, preferably with a low friction coefficient.

Finally, introduction member 20 comprises means for cutting 24 whose function will appear hereafter, of at least the hollow body 21 of the introduction member 20. The means for cutting 24 may then be carried out in any appropriate manner and, according to the example illustrated, include a series of six apertures 24 made at the periphery of hollow body 21, between each of the tubular branches 22, to enable the passage of a cutting tool to provide the cutting of the hollow body 21 according to lines 25 delimited by the mixed dashes in FIG. 6.

Implant 1 is placed inside of hollow body 21 and tubular branches 22, being preferably free inside of the hollow body and of the tubular branches, so that the stress exerted on introduction member 20 is not transmitted to implant 1 itself.

The insertion of implant 1 by means of introduction member 20 thereby formed, is carried out according to the same surgical procedure described above, the removal and cutting of the introduction member 20 occur after the insertion of the whole suspension branches in the patient's body or, more specifically, corresponding tubular branches 22. The removal of the different members of the introduction member 20 by the traction exerted two by two on the opposite tubular branches 22 thereby enables the insertion of implant 1, without any stress, on the introduction member, so that it is found in a state that may be qualified as slack.

In the examples of the treatment and operation described above, the introduction device used comprises simple perforator guides 10. Nevertheless, to try to reduce the trauma by abrasion of the tissue areas crossed to a maximum, it is possible to use an ancillary associating the perforator guide 10 to a soft casing 50 whose shape is complementary to that of guide 10, as illustrated in FIG. 7 and 8 to 10. Casing 50 is inserted on perforator guide 10 that then has a stop device or guard 51 on which casing 50 comes up against during the introduction of perforator guide 10 in the patient's body. Casing 50 is left in the patient's body after removal of perforator guide 10 and before insertion of implant 1, 29, 39. The casing used thereby enables the creation of a channel for the passage of a traction element 23 of the introduction member 20 and wherein a tubular branch 23 and associated suspension strap 3, 4, 5 or a suspension strap 3, 4, 5 may be moved by sliding, so as to adjust the position of implant 1, 29, 39 without abrasion of the tissue crossed. A casing 50 is then used for the insertion of each suspension strap 3, 4, 5. The casings 50 are then removed along with the tubular branches 23 covering the suspension branches of the implant or when the implant is inserted bare after adjusting the implant position.

Thereby, the use of the casings 50 avoids acute inflammatory phenomena and reduces tissue trauma as long as the implant sites consist of very specialised muscle tissue that lost a large part of their ability to quickly regenerate and heal.

Of course, different other modifications may be provided for the invention within the scope of the invention.

What is claimed is:

1. An implant for treatment of cystocele comprising:
   a body-implantable support body made of a bio-compatible material including one of a woven fiber material, a knit fiber material, and a fascia latta and from which extends at least:
   two anterior suspension straps each extending on either side of a sagittal plane, each anterior suspension strap adapted to be fitted into a foramen of a pelvis,
   two posterior suspension straps each extending on either side of a sagittal plane, each posterior suspension strap adapted to be secured to one of ligament and muscle, two middle suspension straps each extending on either side of
      a sagittal plane between the anterior and the posterior straps, each middle suspension strap adapted to be secured to one of ligament and muscle; and
   a device for introduction of the implant into a body, the device comprising an introduction member with a shape that is complementary to that of the implant, the introduction member comprising:
   a hollow body defining a cavity for reception of the support body of the implant,
   tubular branches extending from the hollow body each defining a cavity for reception of one of the suspension straps of the implant,
   means for applying traction extending from an end of each of the branches of the introduction member,
   and means for cutting at least the hollow body of the introduction member.

2. An implant according to claim 1, characterised in that the longitudinal axes of the anterior straps form an angle therebetween exceeding 45°.

3. An implant according to claim 2, characterised in that the angle between the anterior straps is between 100° and 180°.

4. An implant according to claim 2, characterised in that the angle between the anterior straps is between 115° and 170°.

5. An implant according to claim 1 characterised in that the longitudinal axes of the posterior straps form an angle therebetween that is not zero.

6. An implant according to claim 5, characterised in that the angle between the posterior straps exceeds 10°.

7. An implant according to claim 6, characterised in that the angle between the posterior straps is between 10° and 75°.

8. An implant according to claim 6, characterised in that angle between the posterior straps is between 100° and 180°.

9. An implant according to claim 1, characterised in that the longitudinal axis of each middle suspension strap forms, with the anterior part of the sagittal plane, an angle of between 100° and 140°.

10. An implant according to claim 1, characterised in that the length of the anterior straps exceeds 100 mm.

11. An implant according to claim 1, characterised in that the length of the posterior straps exceeds 100 mm.

12. An implant according to claim 1, characterised in that the length of the middle straps exceeds 100 mm.

13. An implant according to claim 1, characterised in that a shape of the support body is substantially rectangular.

14. An implant according to claim 13, characterised in that the length of the support body is between 60 mm and 90 mm and the width is between 40 mm and 60 mm.

15. An implant according to claim 13, characterised in that the anterior straps substantially extend from the anterior corners of the support body.

16. An implant according to claim 1, characterised in that the posterior straps substantially extend from the posterior corners of the support body.

17. An introduction device according to claim 1, characterised in that the means of traction include a semi-rigid needle for each tubular branch.

18. An introduction device according to claim 1, characterised in that the means for cutting comprise at least one aperture for the passage of a cutting instrument.

19. An introduction device according to claim 1, characterised in that it comprises an implant according to claim 1 placed in the cavity of the hollow body and the tubular branches.

20. An introduction device according to claim 19, characterised in that the implant is free inside the introduction device.

21. An introduction device according to claim 1, characterised in that it also comprises an elongated perforator guide or trocar, one end of which is made to be introduced in the patient's body and the other end is equipped with a handle.

22. An introduction device according to claim 21, characterised in that the shape of the perforator guide is curved in one plane.

23. An introduction device according to claim 22, characterised in that the curved part of the perforator extends over an angular sector between 140° and 180°.

24. An introduction device according to claim 22, characterised in that the curved part of the perforator guide has a radius of curvature R of between 30 mm and 60 mm.

25. An introduction device according to claim 21, characterised in that the perforator guide has a helicoid shape at the end opposite to the handle or distal end.

26. An introduction device according to claim 25, characterised in that the distal end of the perforator guide has the shape of a portion of helicoids spire extending over an angle of between 180° and 350°.

27. An introduction device according to claim 26, characterised in that the spire of the perforator guide has a radius of curvature of between 20 mm and 40 mm, with a pitch between 15 mm and 25 mm.

28. An introduction device according to claim 21, characterised in that it also comprises a removable tubular casing whose shape is complementary to that of the perforator guide, intended to be fit on the perforator guide and remain in the patient's body after removal of the perforator guide to define a tunnel for the passage of the means of traction of the introduction member.

* * * * *